United States Patent [19]
Mongeon et al.

[11] Patent Number: 5,620,468
[45] Date of Patent: Apr. 15, 1997

[54] METHOD AND APPARATUS FOR TREATMENT OF ATRIAL FIBRILLATION

[75] Inventors: Luc R. Mongeon; Michael R. S. Hill, both of Minneapolis; Rahul Mehra, Stillwater, all of Minn.

[73] Assignee: Medtronic, Inc., Minneapolis, Minn.

[21] Appl. No.: 627,959

[22] Filed: Apr. 2, 1996

Related U.S. Application Data

[63] Continuation of Ser. No. 230,578, Apr. 21, 1994, abandoned.

[51] Int. Cl.⁶ .................................................. A61N 1/39
[52] U.S. Cl. .................................................. 607/5; 607/14
[58] Field of Search ......................... 607/4–5, 9, 14–15; 128/705

[56] References Cited

U.S. PATENT DOCUMENTS

| | | | |
|---|---|---|---|
| 3,937,226 | 2/1976 | Funke | 128/419 D |
| 4,266,551 | 5/1981 | Stein | 128/419 PG |
| 4,275,737 | 6/1981 | Thompson et al. | 128/419 PG |
| 4,340,062 | 7/1982 | Thompson et al. | 128/419 PG |
| 4,406,286 | 9/1983 | Stein | 128/419 PG |
| 4,407,288 | 10/1983 | Langer et al. | 128/419 PG |
| 4,548,209 | 10/1985 | Wielders et al. | 128/419 D |
| 4,595,009 | 6/1986 | Leinders | 128/419 D |
| 4,649,931 | 3/1987 | Beck | 128/708 |
| 4,693,253 | 9/1987 | Adams | 128/419 D |
| 4,830,006 | 5/1989 | Haluska et al. | 128/419 D |
| 4,880,005 | 11/1989 | Pless et al. | 128/419 PG |
| 4,953,551 | 9/1990 | Mehra et al. | 128/419 D |
| 4,958,632 | 9/1990 | Duggan | 128/419 PG |
| 5,022,395 | 6/1991 | Russie | 128/419 PG |
| 5,161,528 | 11/1992 | Sweeney | 607/5 |
| 5,163,427 | 11/1992 | Keimel | 128/419 D |
| 5,193,536 | 3/1993 | Mehra | 607/4 |
| 5,209,229 | 5/1993 | Gilli | 607/5 |
| 5,243,978 | 9/1993 | Duffin . | |
| 5,267,559 | 12/1993 | Jin et al. | 607/5 |
| 5,269,298 | 12/1993 | Adams . | |
| 5,282,836 | 2/1994 | Kreyenhagen . | |
| 5,314,430 | 5/1994 | Bardy | 607/5 |
| 5,327,900 | 7/1994 | Mason et al. | 128/705 |
| 5,383,910 | 1/1995 | den Dulk | 128/705 |

FOREIGN PATENT DOCUMENTS

| | | | |
|---|---|---|---|
| 0060117 | 9/1982 | European Pat. Off. . | |
| 0095726 | 12/1983 | European Pat. Off. . | |
| 0206248 | 12/1986 | European Pat. Off. . | |
| 0347353 | 12/1989 | European Pat. Off. . | |
| 0420563 | 4/1991 | European Pat. Off. . | |
| 0550344 | 7/1993 | European Pat. Off. . | |
| 0574609 | 12/1993 | European Pat. Off. . | |
| 0588127 | 3/1994 | European Pat. Off. . | |
| 0594271 | 4/1994 | European Pat. Off. . | |
| 0594269 | 4/1994 | European Pat. Off. . | |
| 2528708 | 12/1983 | France . | |
| 9218198 | 10/1992 | WIPO | A61N 1/39 |
| 9306886 | 4/1993 | WIPO . | |
| 9309844 | 5/1993 | WIPO . | |

OTHER PUBLICATIONS

Allessie, et al., "Regional Control of Atrial Fibrillation by Rapid Pacing in Conscious Dogs", *Circulation* 1991;84:1689–1697.

Arzbaecher, et al., "Automatic Tachycardia Recognition", *Pace*, vol. 7, May–Jun., Part II, 1984, pp. 541–547.

Daubert, et al., "Prevention of Atrial Tachyarrhythmias Related to Advanced Interatrial Block by Permanent Atrial Resynchronization", *Pace*, vol. 14, Apr. 1991, part II, pp. 648.

*Primary Examiner*—William E. Kamm
*Attorney, Agent, or Firm*—Reed A. Duthler; Harold R. Patton

[57] ABSTRACT

A method and apparatus for treating fibrillation, particularly atrial fibrillation. In response to detection of fibrillation, a series of low energy pulse bursts is delivered, separated by defined inter-burst intervals, and including bursts unsynchronized to heart depolarizations. Detection of termination of fibrillation during inter-burst intervals results in cancellation of further pulse bursts to prevent reinduction of fibrillation.

26 Claims, 5 Drawing Sheets

METHOD AND APPARATUS FOR TREATMENT OF ATRIAL FIBRILLATION

This application is a continuation of application Ser. No. 08/230,578 filed on 21 Apr. 1994 and now abandoned.

BACKGROUND OF THE INVENTION

This invention relates generally to implantable stimulators and, more specifically, to implantable pacemakers, cardioverters and defibrillators.

Over the years, numerous methods have been proposed for pacing the heart in an attempt to interrupt tachycardias. These include such pacing modalities as overdrive pacing, burst pacing, autodecremental overdrive pacing, and others. These pacing modalities have been formulated to interrupt aberrant reentrant conduction which may lead to sustained tachycardias in one or more chambers of the heart.

It has been proposed that tachycardias could be prevented or interrupted by the use of multi-site cardiac pacing. One early example of multi-site cardiac pacing to terminate or prevent tachyarrhythmia is disclosed in U.S. Pat. No. 3,937,226 issued to Funke. In this device, a number of small surface area pacing electrodes are provided, each coupled to a separate output circuit and amplifier. The disclosed device is equivalent to five or more separate cardiac pacemaker output circuits of conventional design, all adapted to be triggered to pace simultaneously at various locations around the heart. It is hypothesized that by stimulating simultaneously at locations spread around the heart, synchronous with a sensed QRS complex, arrhythmias could be prevented by producing a more nearly simultaneous depolarization of cardiac tissues.

In contrast, fibrillation has generally been treated by means of high energy shocks, which, in the context of implantable anti-arrhythmia devices, are applied by means or large surface area electrodes, including an electrode on or in the chamber to be defibrillated. The high energy level is employed in order to simultaneously depolarize the bulk of the heart chamber to be defibrillated, which will include tissues in all stages of the depolarization-repolarization cycle at the time the pulse is delivered.

In the context of atrial fibrillation, a proposed pacemaker/defibrillator is disclosed in PCT Application No. US 92/02829, Publication No. WO 92/18198 by Adams et al, incorporated herein by reference in its entirety. In this reference careful synchronization of the high voltage atrial defibrillation pulse to the ventricles to avoid induction of ventricular tachycardia or fibrillation is discussed. Delivery of an atrial defibrillation pulse at an inappropriate time may induce ventricular arrhythmias, including ventricular fibrillation.

Use of pacing pulses delivered at multiple sites within the atria to prevent the occurrence of atrial tachyarrhythmias including atrial flutter, which may in some cases progress to atrial fibrillation, has been investigated. For example, the article "Prevention of Atrial Tachyarrhythmias Related to Advanced Interatrial Block by Permanent Atrial Resynchronization, by Daubert et al, Pace, Vol. 14, P. 648, 1991, discloses the use of synchronized pacing pulses delivered to the right and left atria to prevent onset of atrial tachyarrhythmias.

Recently, the theoretical possibility of employing low energy pacing level pulses (i.e. less than 0.05 joules) to terminate fibrillation has been explored. For example, in the recent article "Regional Control of Atrial Fibrillation by Rapid Pacing in Conscious Dogs", by Allessie et al, published in Circulation, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site has been demonstrated. However, the depolarization wavefront created by such pulses does not propagate through the entire chamber, due to the varying polarization states of the tissue surrounding the stimulation site.

Delivery of pulse bursts to the atrium in the presence of atrial fibrillation is disclosed in U.S. patent application Ser. No. 08/082,327, now U.S. Pat. No. 5,356,425, for a "Method and Apparatus for Treatment of Atrial Fibrillation and Flutter, filed Jun. 24, 1993 by Bardy et al. In this device, pulse bursts are delivered in response to detected high ventricular rate, in patients having persistent or frequent atrial fibrillation. The pulse bursts are synchronized to individual depolarizations to stimulate the nerves within the AV nodal fat pad, to produce partial heart block and thus reduce ventricular rate, if required.

Delivery of high frequency pulse bursts to the atrium is also known to induce atrial fibrillation, unless synchronized to atrial depolarizations to assure that the pulse bursts occur within the refractory period of the atrium. This effect is discussed in U.S. patent application Ser. No. 08/086,278, now U.S. Pat. No. 5,334,221, for a Method and Apparatus for Treatment of Angina, filed Jun. 30, 1993 by Bardy, which discloses a device which provides pulse bursts to the atrium, synchronized to detected atrial depolarizations to stimulate the SA nodal fat pad and reduce the sinus rate of patients who suffer from angina.

SUMMARY OF THE INVENTION

The present invention is directed toward providing a method and apparatus for terminating fibrillation using stimulus pulses having energy levels normally associated with cardiac pacing. The invention is believed especially valuable in the context of treating atrial fibrillation, as eliminating the delivery of high energy shocks to the atrium avoids the possibility that such shocks could trigger ventricular tachycardia or fibrillation. In addition, the pain associated with high energy shocks is eliminated.

The present invention surprisingly accomplishes these objectives by applying pulse bursts to the heart, of a type known to induce fibrillation. The pulse bursts comprise series of low energy pulses, typically less than about 50 volts. Each burst cycle may comprise one or more spaced pulse bursts of pulses having a pulse frequency greater than 20 Hz, typically in the range of about 20–200 Hz, continuing over a period of up to several minutes. The first burst in a burst cycle may be delivered asynchronously or synchronously to a sensed atrial depolarization, with subsequent bursts delivered at preset time intervals, asynchronous to later atrial depolarizations. The bursts may have burst durations of about 50 ms or greater, with inter-burst intervals of about one second or greater. During the inter-burst interval, the underlying atrial rhythm is analyzed, with subsequent bursts canceled in response to termination of atrial fibrillation.

In response to failure of a burst cycle to terminate fibrillation, subsequent burst cycles having different pulse frequencies, burst durations or burst inter-burst intervals may be attempted. If the first burst cycle is unsuccessful, multiple burst cycles may be made, with pulse frequency, pulse amplitude, burst duration and/or inter-burst interval varied between successive attempts. In particular, pulse burst parameters may be altered by incrementing the pulse frequency within each burst and increasing the duration of each burst. If a sequence of several burst cycles is unsuccessful, the device may disable the burst function for a period of time, e.g. a few hours or more, and renew attempts to terminate fibrillation thereafter. In some embodiments, the burst therapy may be supplemented by high voltage defibrillation therapy, as a back-up.

It is envisioned that in most patients, the present invention will be practiced in conjunction electrodes located in or on one atrial chamber. However, in some cases, electrodes may be applied to both atria. In the embodiment tested by the inventors, bursts were applied at a single atrial site, using a standard atrial pacing electrode. However, it is believed that the therapy provided by the present invention may also usefully be delivered using multi-site electrode systems or large surface area electrodes. If electrodes are provided at more than one site on the atrium, the bursts may be applied first at one site and, if bursts delivered at that site are unsuccessful in terminating fibrillation, bursts may subsequently be delivered at the other site or sites.

While the invention is believed primarily beneficial in treating atrial fibrillation, as a practical matter, it may be difficult to distinguish atrial fibrillation from atrial flutter, and fibrillation and flutter may be simultaneously present in some patients. Furthermore, it is believed possible that the therapy may also be beneficial in treating rhythms which physicians might identify as atrial flutter, without accompanying atrial fibrillation. It is thus believed likely that the present invention may be employed in a device which delivers the burst therapy in response to a detected atrial rhythm above a preset rate, for example, a rate above 240 b.p.m.

Unlike the method of pacing fibrillating tissue disclosed in the above-cited Allessie article, the efficacy of the present invention does not depend upon precisely synchronizing individual pulses to the detected heart rhythm. Unlike high voltage defibrillation, the therapy provided by the present invention is not based upon the premise that a single delivered pulse will result in simultaneous depolarization of the entire fibrillating chamber, and does not raise a corresponding risk of induction of ventricular tachyarrhtmia.

In commercial implementations of the invention, the invention may be embodied as part of an implantable pacemaker/cardioverter/defibrillator system. In this case, large surface area electrodes may also be present and may be employed for cardioversion or defibrillation in the event pacing therapies fail to terminate the detected arrhythmia. Alternatively, the invention may be embodied as an atrial pacemaker only, and the electrodes in such case would be employed only for delivery of pacing pulses and burst pulses. In either embodiment, the large surface area electrodes may also be employed to provide anti-tachycardia pacing as in the Duffin patent and/or to prevent the occurrence of atrial fibrillation as described in the above-cited article by Dauberr et al.

DETAILED DESCRIPTION OF THE PREFERRED EMBODIMENT

Figure 1:
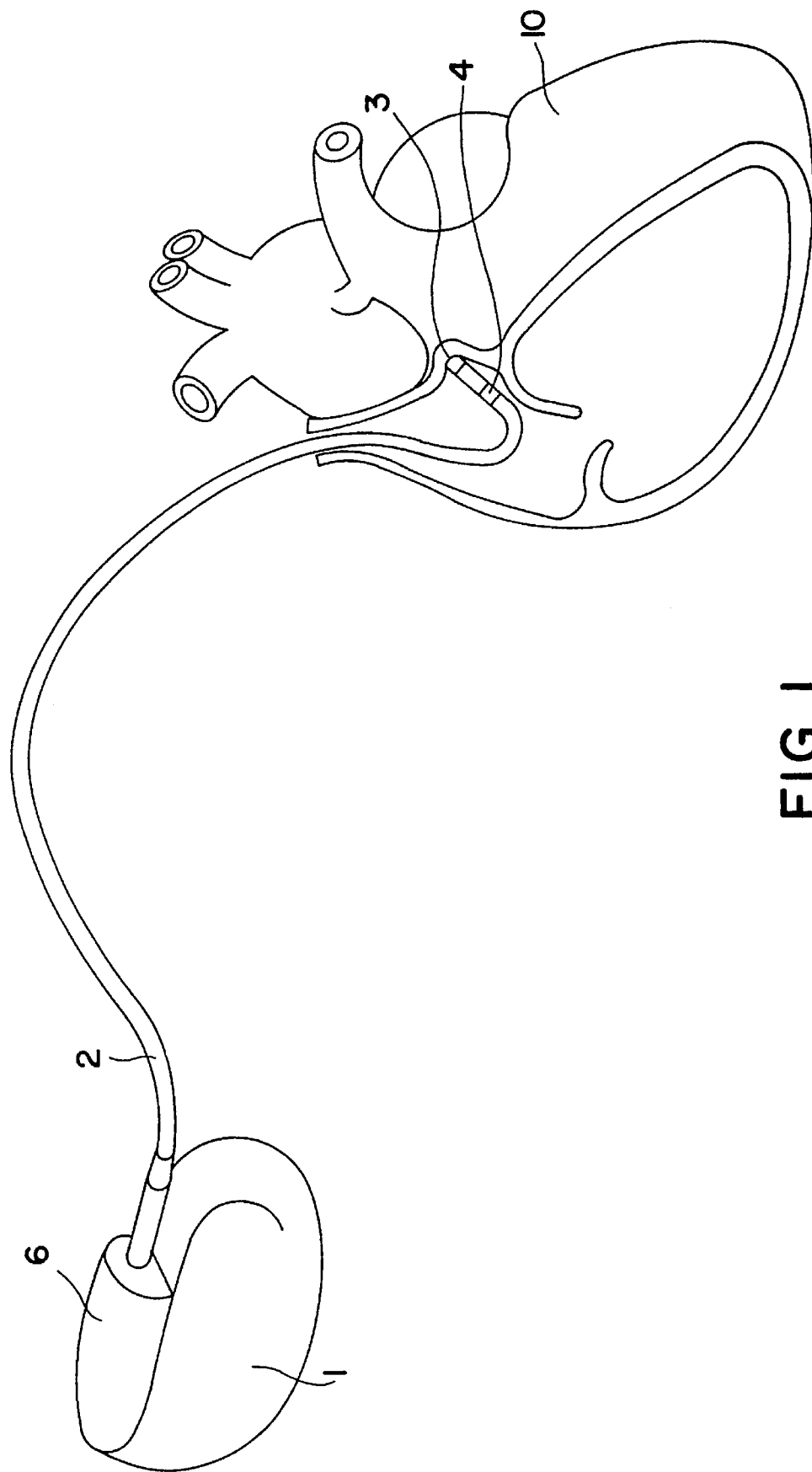
FIG. 1 is a plan view of an implantable pacemaker and a first associated lead of the type in which the present invention may be embodied, illustrating the location of the lead and its electrodes in relation to a human heart.

FIG. 1 is a plan view of an implantable pacemaker 1 and its associated lead system, in conjunction with a human heart 10. As illustrated, the device includes a right atrial lead 2 provided with pacing electrodes 3 and 4. Lead 2 may be a conventional bipolar atrial pacing lead, serving to perform normal cardiac pacing functions, to sense atrial depolarizations and to deliver burst pulses. Alternatively, one or all of cardiac pacing, sensing of atrial depolarizations or burst pulse delivery may be accomplished between one electrode located on lead 2 and an electrode located on the housing of the device 1. Similarly, one or more epicardial electrodes may be employed instead if desired. While the electrodes as illustrated take the form of a single pair of pacing electrodes, only one of which (electrode 3) is employed to stimulate heart tissue, a bipolar pair including an electrode on each atrium, multiple electrode pairs, or large surface epicardial or transvenous electrodes located on one or both atria might alternatively be employed to deliver the burst pacing therapy of the present invention.

For purposes of the present invention, it is envisioned that the electrodes located on the right atrial lead 2, or a corresponding epicardial electrode or electrodes will be used for routine AAI pacing in the presence of bradycardia, and optionally for sensor based rate responsive AAIR mode cardiac pacing and/or anti-tachycardia pacing. In response to detection of atrial fibrillation, delivery of the pulse bursts is initiated. In response to detection of atrial fibrillation, the pacemaker delivers an initial pulse burst which may be synchronized or unsynchronized to a detected atrial depolarization, and during the following inter-burst interval monitors the atrial electrogram to determine whether atrial fibrillation has terminated. If fibrillation has terminated, burst delivery is also terminated, to avoid re-induction of fibrillation by subsequent pulse bursts. Otherwise, if the burst cycle includes more than one burst, the next burst is delivered at the end of the inter-burst interval, irrespective of the timing of atrial depolarizations occurring during the inter-burst interval. Burst delivery is continued until either the end of the defined burst cycle or detection of termination of atrial fibrillation.

It is not envisioned that the burst pulse therapy provided by the present invention will be successful to terminate all atrial fibrillation episodes in any single patient. Unlike ventricular fibrillation, atrial fibrillation is not an immediately life threatening condition. Repeated termination attempts can be undertaken without severe consequences. If the first burst cycle is unsuccessful, multiple burst cycles may be made, with pulse frequency, pulse amplitude, burst duration and/or inter-burst interval varied between successive attempts. In particular, pulse burst parameters may be altered by incrementing the pulse frequency within each burst and increasing the duration of each burst. If a sequence of several burst cycles is unsuccessful, the device may disable the burst function for a period of time, e.g. a few hours or more, and renew attempts to terminate fibrillation thereafter. If the invention is embodied in a device which also includes high voltage atrial defibrillation capabilities, the pacing level therapy of the present invention may be employed as an initial therapy for atrial fibrillation, with the intended goal of simply reducing the number of high voltage shocks given.

Figure 2:
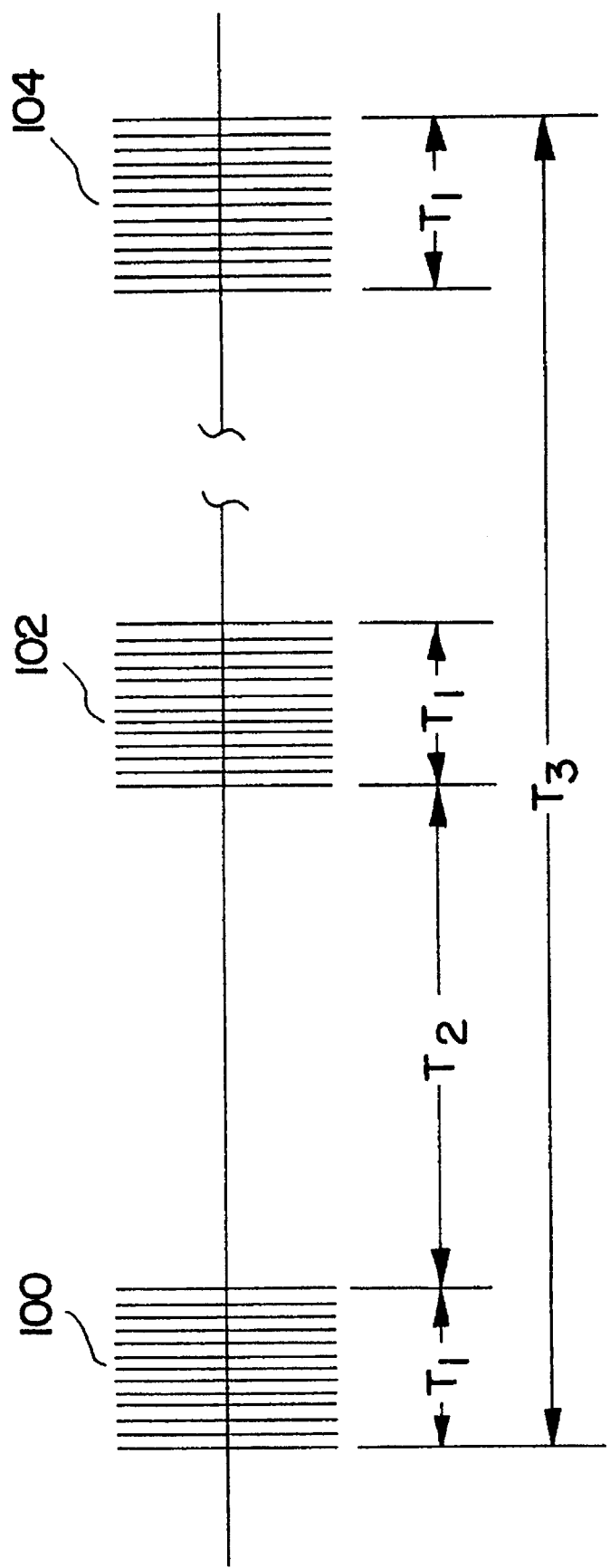
FIG. 2 is an illustration of a burst cycle provided by the present invention.

FIG. 2 illustrates the basic timing intervals associated with a single burst cycle. Three representative bursts are illustrated at 100, 102 and 104. The delivered bursts extend over a burst cycle length $T_3$, which includes a series of bursts having a burst duration $T_1$, separated from the next subsequent burst by an inter-burst interval $T_2$. The duration $T_3$ of the burst cycle may be predefined, or it may occur as a result of the delivery of a predetermined number of bursts, the duration of $T_3$ being dependent upon the number of bursts to be delivered, burst duration ($T_1$) and inter-burst interval ($T_2$).

The efficacy of the pulse burst therapy of the present invention was tested by the inventors by first inducing atrial fibrillation in a dog by means of 65 hertz pulse bursts from an Itrel II neurostimulator, manufactured by Medtronic, Inc., Minneapolis, Minn., applied to the atrium of a dog by means of an atrial pacing lead. Pulse bursts of 50 and 130 hertz from the same stimulator were tested and found, in some cases, to be effective terminating atrial fibrillation. It should be noted that successive pulse bursts applied after termination of fibrillation often reinitiated fibrillation, emphasizing the importance of determining, during the inter-burst interval, whether atrial fibrillation has terminated and of preventing delivery of subsequent pulse bursts if fibrillation has in fact terminated.

Figure 3:
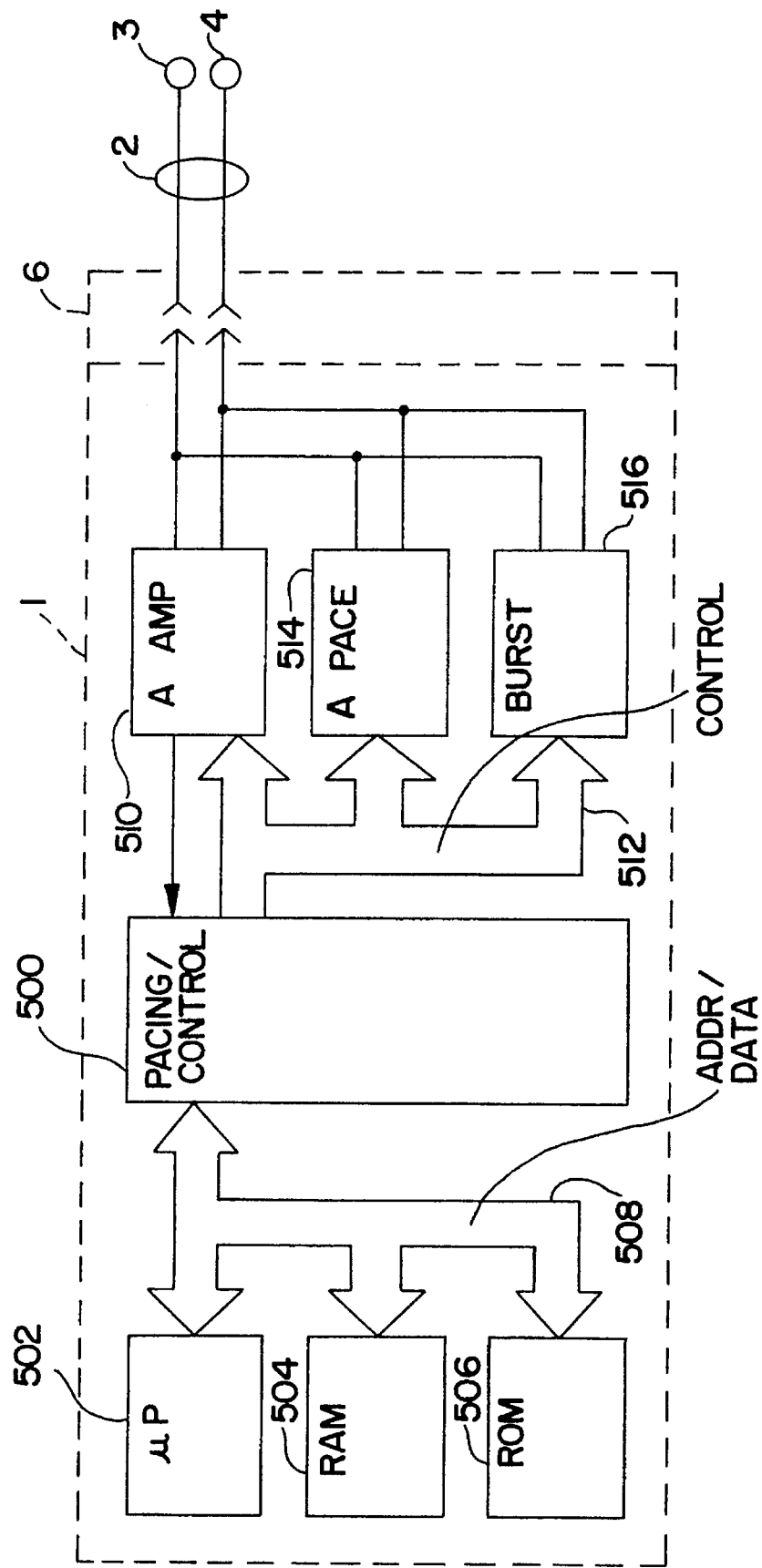
FIG. 3 is block diagram of a pacemaker, in which the present invention is incorporated, allowing delivery of burst pulses.

FIG. 3 is a block diagram illustrating the major functional components of the implantable pacemaker 1, illustrated in FIG. 1. Timing and control functions are preferably accomplished using a microprocessor based system, corresponding to those used in presently available pacemakers. The basic function and operation of the timing and control logic 500, microprocessor 502, random access memory 504 and read only memory 506 may correspond to corresponding elements in the microprocessor controlled pacemaker systems disclosed in U.S. Pat. No. 4,407,288 issued to Langer et al. on Oct. 4, 1983, U.S. Pat. No. 5,022,395, issued to Russie on Jun. 11, 1991, U.S. Pat. No. 4,958,632 issued to Duggan on Sep. 25, 1990 or in U.S. Pat. No. 4,830,006 issued to Haluska et al. on May 16, 1989, all of which are incorporated herein by reference in their entireties. Timing/control circuitry 500, in conjunction with microprocessor 502 detects the occurrence of bradycardia and/or tachycardia and in response thereto controls the delivery of the various pacing therapies available via control bus 512. Microprocessor 502 also detects the occurrence of atrial fibrillation based on sensed atrial depolarizations and controls delivery of pulse bursts by burst pulse generator 514. The operation of microprocessor 502 is controlled by programming stored in read only memory 506 and in random access memory 504. The operation of the device may be altered by the physician by altering the programming stored in memory 504, using control and telemetry circuitry conventional in implantable stimulators. Memory 504 may also be employed for storing measured parameters such as P-P intervals, and P-wave widths and amplitudes. Memory 504 may also be employed to store digitized electrocardiograms sensed using the various electrodes provided. Communication to and from the microprocessor 502, memories 504 and 506 and control logic 500 is accomplished using address/data bus 508.

For purposes of applying the pulse burst anti-fibrillation therapy of the present invention, pulse frequencies of 20–200 Hz are preferably available in conjunction with burst durations of 100 milliseconds to 10 seconds and inter-burst intervals of 2 seconds to 60 seconds, delivered over burst cycle times of 1–5 minutes. The specific burst pulse parameters, or sets of parameters if multiple burst cycles are employed, may be selected by the implanting physician.

In a preferred embodiment of the device, the microprocessor sets the duration of the bursts in at least the first burst cycle as a function of the cycle length of the detected tachyarrhythmia. For example, the initial burst duration may be set to equal a multiple of the cycle length or may be set to equal the cycle length plus a fixed increment. For example, in response to a fibrillation having a rate of 300 b.p.m. (cycle length 200 ms), an initial burst duration of twice the cycle length (400 ms) may be selected, or a burst duration equal to the cycle length plus 150 ms (350 ms) may be selected.

As the delivered pulse bursts are not required to be delivered synchronized to the atrial tissue adjacent the sensing electrodes, the burst cycle can be initiated at any convenient time following detection of atrial fibrillation. Alternatively, the first burst in each cycle may be synchronized to a detected atrial depolarization, with the rest of the bursts in the burst cycle, if provided, being delivered at the specified inter-burst intervals.

Following delivery of each burst, the microprocessor analyzes the atrial electrogram provided by atrial amplifier 510 to determine whether fibrillation has terminated. If so, the burst pulses are terminated. If fibrillation persists, the next burst is delivered at expiration of the inter-burst interval. Delivery of bursts continues until the burst cycle ends, due either to expiration of the cycle time or delivery of the number of bursts specified for the burst cycle. If the first burst cycle is unsuccessful, multiple burst cycles may be made, with pulse frequency, pulse amplitude, burst duration and/or inter-burst interval varied between successive attempts. In particular, pulse burst parameters may be altered by incrementing the pulse frequency within each burst and increasing the duration of each burst. If a specified number of burst cycles is delivered without termination, the burst therapy is preferably disabled for a period of time, e.g. one hour or more, to prevent excessive battery drain.

Atrial sensing circuit 510 be any conventional cardiac sense amplifier circuits equivalent to any prior art atrial cardiac sensing circuits employed in previous devices. For example, the sensing circuit may correspond to the circuit disclosed in U.S. Pat. No. 4,266,551 issued to Stein on May 21, 1981, U.S. Pat. No. 4,275,737 issued to Thompson et al, U.S. Pat. No. 4,649,931 issued to Beck on Mar. 17, 1987, all of which are incorporated herein by reference in their entireties.

The burst pulse output circuitry 516 may correspond generally to the output circuitry employed in commercially available implantable neurostimulators, such as employed in the Medtronic Itrel II nerve stimulator, discussed above. Alternatively, burst pulse generation circuitry as provided by the Medtronic Model 2349 Programmable stimulator may be employed. Numerous commercially available medical stimulators have pulse generation circuitry which may be employed or adapted to practice the present invention, and, for purposes of the present invention, any circuit capable of generating pulse bursts of the frequencies, widths and amplitudes specified above should be sufficient. While the inventors have employed biphasic pulses, as delivered by the Itrel II device, it is believed that monophasic or other multiphasic pulses may also usefully be employed. More specifically, circuits capable of generating pulses at an amplitude of 5 to 15 volts, with a pulse width of about 0.1 millisecond to about 5 milliseconds should be sufficient, although higher amplitudes may be required in some patients. The Itrel II device employed by the inventors has a maximum pulse width of 0.45 ms and a maximum pulse amplitude of 10.5 volts. Other low energy pulses (i.e. 0.05 joules or less) having parameters outside these values may also be employed.

The pacing output circuitry 514 may correspond generally to the output circuitry illustrated in U.S. Pat. No. 4,406,286 issued to Stein on Sep. 27, 1983 or U.S. Pat. No. 4,340,062 issued to Thompson et at. on Jul. 20, 1982, both of which are also incorporated herein by reference in their entireties.

Atrial sense amp circuitry 510 is coupled to fight atrial lead 2 and to a pair of electrodes 3 and 4, located adjacent to distal end of the lead. Alternatively, sense amp circuit 510 may be coupled to only one of the electrodes 3 and 4, and may sense between that electrode and the conductive housing of the implantable device or one of the large surface electrodes.

Atrial anti-tachycardia and anti-bradycardia pacing therapies may optionally be delivered by the device and may include those described in U.S. Pat. No. 4,880,005 by Pless, cited above. A device generally as disclosed in the Pless et al patent may serve as a practical starting point for practicing the invention, with burst pulse generation circuit 516 and software in ROM 506 for controlling atrial fibrillation detection and burst pulse delivery added.

Detection of atrial fibrillation may be accomplished by microprocessor 502 using any of the various detection methodologies known to the art. Generally, atrial fibrillation may be detected in response to an extended series of high rate (e.g. 240 b.p.m. or greater) atrial depolarizations. If greater specificity for atrial fibrillation is desired, analysis of regularity of rate waveform morphology may also be employed. Termination of atrial fibrillation may be detected in response to a decrease in the rate of atrial depolarizations and/or an increase in their regularity. Appropriate detection methodologies are disclosed in the above-cited PCT application by Adams et al, and in the article "Automatic Tachycardia Recognition", by Arzbaecher et al, published in Pace, Vol. 7, May–June 1984, part II, pages 541–547, both incorporated herein by reference in their entireties.

Figure 4:
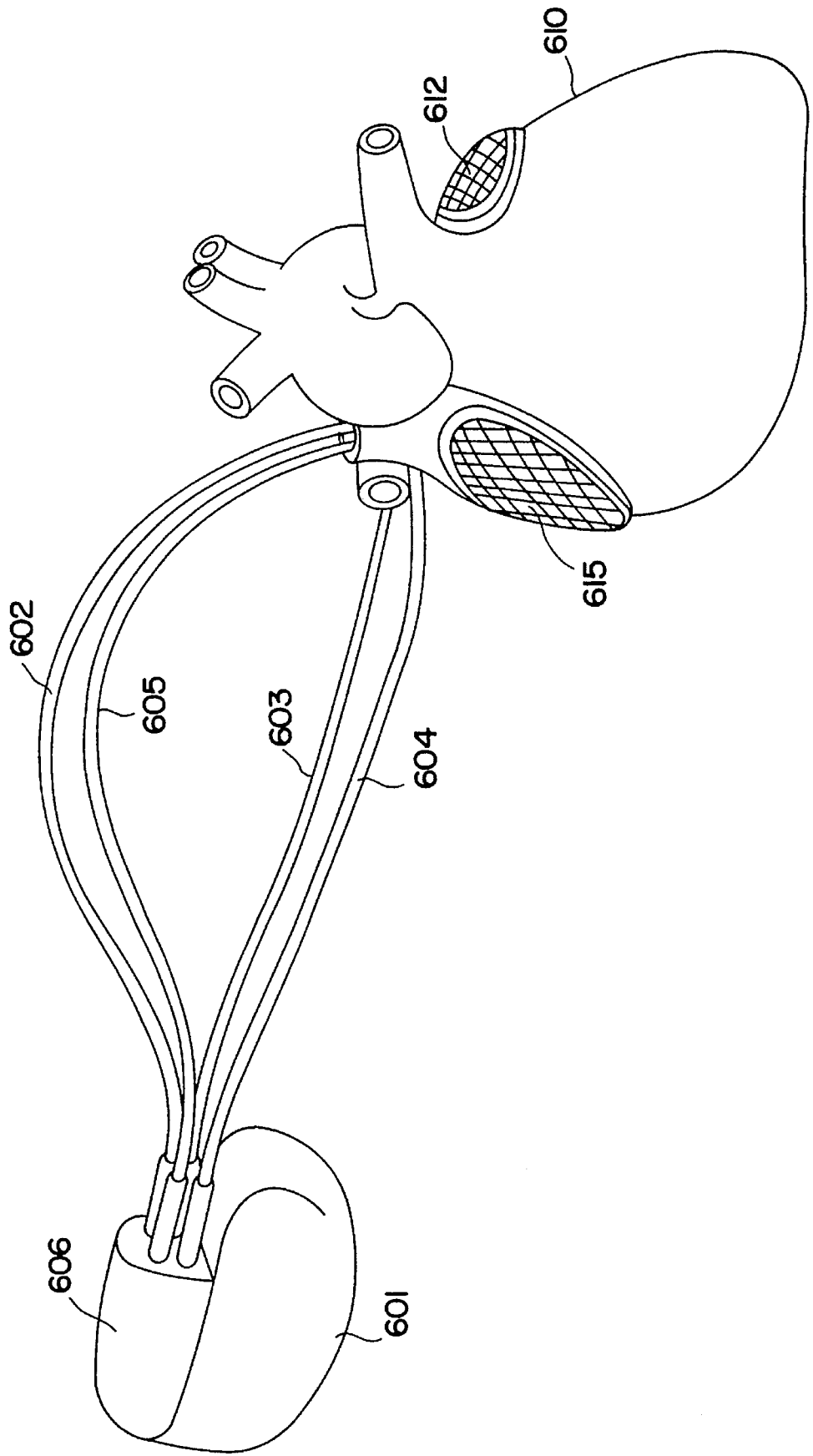
FIG. 4 is a plan view of an implantable pacemaker/cardioverter/defibrillator and an associated lead system of the type in which the present invention may be embodied, illustrating the location of the leads and electrodes in relation to a human heart.

FIG. 4 is an illustration of a pacemaker/cardioverter/ defibrillator 601 and an associated lead system, in conjunction with a human heart 610. As illustrated, the device includes a right atrial lead 602, a right ventricular lead 605 and two epicardial electrode leads, 603 and 604. Leads 603 and 604 carry large surface defibrillation electrodes 612 and 615 and may correspond to any of the commercially available ventricular defibrillation electrodes presently available, downsized for atrial application. Alternatively, endocardial defibrillation leads as described in the above-cited PCT application by Adams et al may be employed. Leads 602 ad 605 are both bipolar pacing leads, and may correspond to any of the numerous leads presently available commercially. The electrode pair 608, 610 located at the distal end of lead 602 is located in the right atrium. The electrode pair 614, 616 located at the distal end of electrode lead 605 is located in the right ventricle. For purposes of the present invention, it is envisioned that electrodes located on lead 605 will be employed for ventricular bradycardia pacing and sensing and that the electrodes located on lead 602 will be employed for atrial pacing and sensing functions, as well as for burst pulse delivery. However, as noted above, in alternate embodiments, other atrial electrodes may be employed to deliver pulse bursts, including electrodes 612 and 615. The device may operate to provide DDD mode pacing employing pacing of both the atrial and ventricular chambers, or to simply provide ventricular bradycardia pacing. Similarly, the electrodes located on lead 602 may be employed to provide anti-tachycardia pacing in the atrium, if desired.

In response to detection of atrial fibrillation, the device delivers pulse bursts as discussed in conjunction with the pacemaker illustrated in FIG. 1. In addition, in response to failure of delivered pulse bursts to terminate atrial fibrillation, high voltage pulses may be delivered to electrodes 603 and 604 to defibrillate the atrium as described in the cited PCT application by Adams et al.

Figure 5:
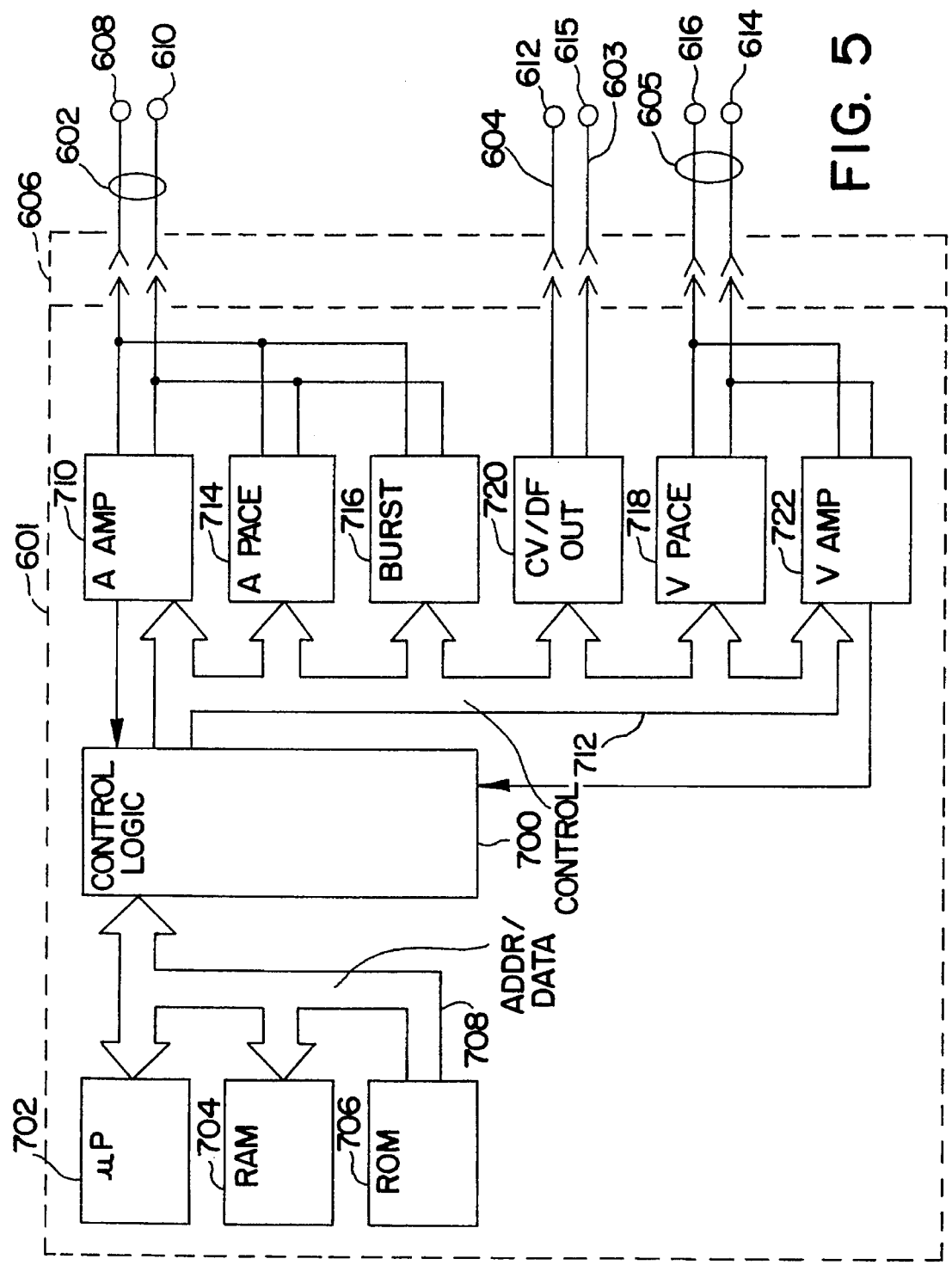
FIG. 5 is block diagram of a implantable pacemaker/cardioverter/defibrillator in which the present invention is incorporated, allowing delivery of burst pulses.

FIG. 5 is a block diagram illustrating the major functional components of the implanted pacemaker/cardioverter/ defibrillator 601 illustrated in FIG. 4. Timing and control functions are preferably accomplished using a microprocessor based system, corresponding to those used in presently available pacemaker/cardioverter/defibrillator systems. The basic function and operation of the timing and control logic 700, microprocessor 702, random access memory 704 and read only memory 706 may correspond to corresponding elements in the microprocessor controlled systems disclosed in U.S. Pat. No. 4,407,288 issued to Langer et al. on Oct. 4, 1983, U.S. Pat. No. 5,022,395, issued to Russie on Jun. 11, 1991, U.S. Pat. No. 4,958,632 issued to Duggan on Sep. 25, 1990 or in U.S. Pat. No. 4,830,006 issued to Haluska et al. on May 16, 1989, all of which are incorporated herein by reference in their entireties. Timing/control circuitry 700, in conjunction with microprocessor 702 detects the occurrence of bradycardia and/or tachycardia and in response thereto controls the delivery of the various pacing, cardioversion and alefibrillation therapies available via control bus 712. The operation of microprocessor 702 is controlled by programming stored in read only memory 706 and in random access memory 704. The operation of the device may be altered by the physician by altering the programming stored in memory 704, using control and telemetry circuitry conventional in implantable stimulators. Memory 704 may also be employed for storing measured parameters, such as R-R intervals, P-P intervals, P-R intervals and P or R-wave widths and amplitudes. Memory 704 may also be employed to store digitized electrocardiograms sensed using the various electrodes provided. Communication to and from the microprocessor 702, memories 704 and 706 and control logic 700 is accomplished using address/data bus 708.

In the context of the present invention, it is envisioned that the high voltage cardioversion and defibrillation therapies provided may simply correspond to those available in the prior art. High voltage atrial defibrillation/cardioversion pulses are provided by the Defib/CV output circuit 720, under control of timing/control circuitry 700. Typically, this circuit will be capable of charging and discharging high voltage capacitors therein to produce output pulses in excess of 300 volts into a 50 ohm load. In any case, the circuit 722 should be capable of delivering pulses well in excess of 0.2 joules. Examples of appropriate circuitry for accomplishing the generation of cardioversion and defibrillation pulses are set forth in U.S. Pat. No. 4,595,009 issued to Leinders on Jun. 17, 1986, U.S, Pat. No. 4,548,209 issued to Wielders on Oct. 22, 1985, U.S. Pat. No. 4,693,253 issued to Adams on Sep. 15, 1987, U.S. Pat. No. 4,953,551 issued to Mehra et al.

on Sep. 4, 1990, or U.S. Pat. No. 5,163,427 issued to Keimel, all of which are also incorporated herein by reference in their entireties. For purposes of the present invention, it is believed that any prior an defibrillation/cardioversion output circuit may be usefully employed.

Atrial and ventricular sensing circuits 710 and 722 may be conventional cardiac sense amplifier circuits equivalent to any prior art cardiac sensing circuits employed in previous devices, as discussed above in conjunction with amplifier 510, FIG. 6. Low impedance pacing output circuitry 714 similarly corresponds to output circuit 514, FIG. 6.

Ventricular sense amp circuitry 722 is coupled to right ventricular lead 605, and to a pair of electrodes 614 and 616, located adjacent to distal end of the lead. Alternatively, sense amp circuit 722 may be coupled to only one of the electrodes 614 and 616, and may sense between that electrode and the conductive housing of the implantable device or one of the large surface electrodes.

Similarly, atrial sense amp circuitry 710 is coupled to right atrial lead 602, and to a pair of electrodes 608 and 610, located adjacent to distal end of the lead. Alternatively, sense amp circuit 710 may be coupled to only one of the electrodes 608 and 610, and may sense between that electrode and the conductive housing of the implantable device or one of the large surface electrodes.

Ventricular bradycardia pacing and atrial cardioversion, and defibrillation therapies may correspond to any prior art implantable pacemaker/cardioverter/defibrillator, in particular, a device as disclosed in the above-cited PCT Patent Application by Adams et al may serve as the starting point for practicing the invention, with burst pulse generation circuit 716 and software in ROM 706 for controlling atrial fibrillation detection and burst pulse delivery added, as discussed in conjunction with FIG. 3. Operation of the device in response to detection of atrial fibrillation corresponds to that of the device of FIG. 3, with the exception that, if the physician so desires, high voltage defibrillation pulses may be delivered following failure of a predefined number of pulse cycles to terminate atrial fibrillation.

While the pulse burst therapy provided by the present invention does consume more energy than a typical bradycardia pacemaker, the overall energy delivered by means of the pulse bursts need not be substantial as compared to the delivery of a cardioversion or defibrillation pulse. It is believed that in most cases, pulse energies of 5 millijoules or less should be sufficient. In many cases, it is believed that therapy can be accomplished individual pulses having energy levels of less than 1 millijoule. For example, delivery of a 5 volt pulse into a 100 ohm load, using a 0.5 millisecond pulse width results in the expenditure of only 0.5 millijoules per pulse. Thus, while the therapy of the present invention consumes more energy than bradycardia pacing, it should not pose a significant problem for occasionally activated pulse regimens.

In conjunction with the above disclosure, we claim:

1. An anti-arrhythmia device, comprising:

means for detecting atrial fibrillation in a patient's heart;

electrode means for delivering pulse bursts to said patient's heart;

pulse generator means responsive to detection of atrial fibrillation for delivering series of low energy pulse bursts unsynchronized to depolarizations of said patient's heart to said electrode means.

2. An anti-arrhythmia device, comprising:

means for detecting atrial fibrillation in a patient's heart;

electrode means for delivering low energy pulse bursts to said patient's heart; and pulse generator means responsive to detection of atrial fibrillation for delivery to said electrode means of a series of low energy pulse bursts which are separated by predefined inter-burst intervals and are unsynchronized to depolarizations of said patient's heart.

3. An anti-arrhythmia device, comprising:

means for detecting atrial fibrillation in a patient's heart;

electrode means for delivering low energy pulse bursts to said patient's heart;

pulse generator means responsive to detection of atrial fibrillation for delivery of series of pulse bursts to said electrode means separated by predefined inter-burst intervals;

means for detecting termination of fibrillation during said inter-burst intervals; and means responsive to termination of fibrillation for terminating delivery of said pulse bursts.

4. Apparatus according to claim 1 or claim 2 or claim 3 wherein said pulse generator means comprises means for delivering pulse bursts having pulse frequencies of 20 Hz or more.

5. Apparatus according to claim 3 further comprising means responsive to delivery of a series of said pulse bursts in an absence of detected termination of fibrillation, for disabling said pulse generator means for a predefined period of time.

6. Apparatus according to claim 3, further comprising means for altering parameters of said pulse bursts in an absence of detected termination of fibrillation.

7. Apparatus according to claim 3, further comprising means for increasing durations of said pulse bursts in an absence of detected termination of fibrillation.

8. Apparatus according to claim 3, further comprising means for increasing frequency of pulses within said pulse bursts in an absence of detected termination of fibrillation.

9. An anti-arrhythmia device, comprising:

means for detecting depolarizations of a patient's heart at a rate in excess of a predetermined rate, said predetermined rate being at least 240 beats per minute;

electrode means for delivering pulse bursts to said patient's heart;

pulse generator means responsive to detection of depolarizations at a rate in excess of said predetermined rate, for delivering low energy pulse bursts having pulse frequencies of 20 Hz or greater to said electrode means.

10. An anti-arrhythmia device, comprising:

means for detecting atrial fibrillation in a patient's heart;

electrode means for delivering low energy pulse bursts to said patient's heart;

pulse generator means responsive to detection of atrial fibrillation in said patient's heart, for delivering pulse bursts having a pulse frequency of 20 Hz or greater to said electrode means.

11. An anti-arrhythmia device, comprising:

means for determining cycle lengths of a patient's heart rhythm;

means for detecting heart rhythms having short cycle lengths in a patient's heart;

electrode means for delivering low energy pulse bursts to said patient's heart;

pulse generator means responsive to detection of said heart rhythms, for delivering pulse bursts having a pulse frequency of 20 Hz or higher frequencies, having burst durations longer than said determined cycle lengths and having predefined inter-burst intervals to said electrode means.

12. Apparatus according to claim 1 or claim 2 or claim 3 or claim 9 or claim 10 or claim 11 wherein said pulse generator means comprises means for delivering pulse bursts having pulse amplitudes of 50 volts or less.

13. Apparatus according to claim 1 or claim 2 or claim 3 or claim 9 or claim 10 or claim 11 wherein said pulse generator means comprises means for delivering pulse bursts having pulse energies of 0.05 joules or less.

14. A method of treating atrial fibrillation, comprising:

applying an electrode to a patient's heart;

detecting atrial fibrillation in said patients heart;

responsive to detection of atrial fibrillation, delivering series of low energy pulse bursts unsynchronized to depolarizations of said patient's heart to said electrode.

15. A method of treating atrial fibrillation, comprising:

applying an electrode to a patient's heart;

detecting atrial fibrillation in said patients heart;

responsive to detection of atrial fibrillation, delivering to said electrode low energy pulse bursts which are separated by predefined inter-burst intervals, and are unsynchronized to depolarizations of said patient's heart.

16. A method of treating atrial fibrillation, comprising:

applying an electrode to a patient's heart;

detecting atrial fibrillation in said patients heart;

responsive to the detection of atrial fibrillation, delivering low energy pulse bursts to said electrode, separated by predefined inter-burst intervals, detecting termination of fibrillation during said inter-burst intervals; and responsive to termination of fibrillation, terminating delivery of said pulse bursts.

17. A method according to claim 14 or claim 15 or claim 16 wherein pulse burst delivery step comprises delivering pulse bursts having pulse frequencies of 20 Hz or greater.

18. A method according to claim 16 further comprising suspending delivery of said pulse bursts for a predefined period of time absent detected termination of fibrillation.

19. A method according to claim 16, further comprising altering parameters of said pulse bursts in an absence of detected termination of fibrillation.

20. A method according to claim 16, further comprising increasing frequency of pulses within said pulse bursts in an absence of detected termination of fibrillation.

21. A method according to claim 16, further comprising increasing duration of said pulse bursts in an absence of detected termination of fibrillation.

22. A method of treating arrhythmia, comprising:

applying an electrode to a patient's heart;

detecting depolarizations of said patient's heart at a rate in excess of a predetermined rate, said predetermined rate being at least 240 beats per minute;

responsive to detection of depolarizations at a rate in excess of said predetermined rate, delivering low energy pulse bursts having a pulse frequency of 20 Hz or greater to said electrode.

23. A method of treating atrial fibrillation, comprising:

applying an electrode to a patient's heart;

detecting atrial fibrillation in said patient's heart;

responsive to detection of atrial fibrillation in said patient's heart, for delivering low energy pulse bursts having a pulse frequency of 20 Hz or greater to said electrode.

24. An method of treating tachyarrhythmias, comprising:

applying an electrode to a patient's heart;

determining cycle lengths of said patient's heart rhythm;.

detecting heart rhythms having short cycle lengths in said patient's heart;

responsive to detection of fibrillation in said patient's heart, delivering pulse bursts having a pulse frequency of 20 Hz or higher frequencies, having burst durations longer than said determined cycle lengths and having predefined inter-burst intervals to said electrode.

25. A method according to claim 14 or claim 15 or claim 16 or claim 22 or claim 23 or claim 24 wherein said pulse burst delivery step comprises delivering pulse bursts having pulse amplitudes of 50 volts or less.

26. A method according to claim 14 or claim 15 or claim 16 or claim 22 or claim 23 or claim 24 wherein said pulse burst delivery step comprises delivering pulse bursts having pulse energies of 0.05 joules or less.

* * * * *